United States Patent [19]

Garfield et al.

[11] Patent Number: 5,450,857
[45] Date of Patent: Sep. 19, 1995

[54] METHOD FOR THE DIAGNOSIS OF CERVICAL CHANGES

[75] Inventors: R. E. Garfield, Friendswood; W. S. Glassman, Houston, both of Tex.

[73] Assignee: Board of Regents, The University of Texas System, Austin, Tex.

[21] Appl. No.: 246,060

[22] Filed: May 19, 1994

[51] Int. Cl.⁶ ............................................. A61N 1/00
[52] U.S. Cl. .................................. 128/778; 128/774; 128/775
[58] Field of Search ............... 128/774, 775, 778, 665; 604/264, 280, 283; 606/3, 10, 13

[56] References Cited

U.S. PATENT DOCUMENTS

| | | | |
|---|---|---|---|
| 4,476,871 | 10/1984 | Hon | 128/775 X |
| 4,498,481 | 2/1985 | Lemke . | |
| 4,782,819 | 11/1988 | Adair | 604/264 X |
| 5,135,006 | 8/1992 | Bellinson | 128/775 |
| 5,167,237 | 12/1992 | Rabin et al. | 128/778 X |
| 5,184,619 | 2/1993 | Austin | 128/775 X |
| 5,279,308 | 1/1994 | Disabito et al. | 128/775 |
| 5,348,018 | 9/1994 | Alfano et al. | 606/3 X |

OTHER PUBLICATIONS

Patent disclosure for "Method and Apparatus Using Laser Fluoroescence Spectroscopy for Human Spermatozoa Diagnosis", by Alfano et al., May 25, 1989.

Chwalisz, K., "The use of progesterone antagonists for cervical ripening and as an adjunct to labour and delivery", Progesterone Antagonists in Reproductive Medicine and Oncology, *Human Reproduction,* 9(1):131–161, 1994, Beier and Spitz, eds., Oxford Univ. Press, Oxford, UK.

Fosang and Handley, "Connective Tissue Remodelling in the Ovine Cervix During Pregnancy and At Term", *Conn. Tissue Res.,* 17:277–285, 1988.

Garfield et al., "Effects of the Antiprogesterone RU 486 on Preterm Birth in the Rat", *Am. J. Obstet. and Gynecol.,* 157(5):1281–1285, 1987.

Garfield and Baulieu, "The antiprogesterone steroid RU 486: a short pharmaceutical and clinical review, with emphasis on the interruption of pregnancy", *Bail-liere's Clin. Endocrinology and Metabolism,* 1(1):207–221, 1987.

Glassman et al., "Excitation Spectroscopy of Malignant and Non-malignant Gynecological Tissues", *Lasers in the Life Sciences,* 6(2):99–106, 1994.

Glassman, W. S., "Fluorescence Spectroscopy of Human Nonmalignant and Malignant Cells and Tissues", Dialog Abstract No. 01308565.

Glassman, et al., "Ultraviolet Excited Fluorescence Spectra from Non-malignant and Malignant Tissues of the Gynecological Tract", *Lasers in the Life Sciences,* 5(1–2):49–58, 1992.

Granström, et al., "Insufficient remodelling of the uterine connective tissue in women with protracted labour", *Brit. J. Obstet. & Gynecol.,* 98:1212–1216, 1991.

Granström, et al., "Changes in the connective tissue of corpus and cervix uteri during ripening and labour in term pregnancy", *Brit. J. Obstet. & Gynecol.,* 96:1198–1202, 1989.

Koenyesi and Woessner, J., "Effects of Hormonal Perturbations on The Small Dermatan Sulfate Proteoglycan and Mechanical Properties of the Uterine Cervix of Late Pregnant Rats", *Connective Tissue Res.,* 199–205, 1991.

(List continued on next page.)

Primary Examiner—Sam Rimell
Attorney, Agent, or Firm—Arnold, White & Durkee

[57] ABSTRACT

The present invention relates to a method and instrumentation for detecting the changes in cervical connective tissues associated with cervical dilation or effacement. This method uses an optical system to determine changes by laser or other light induced native fluorescence spectroscopies (LIF) of cervix. The method is non-invasive and instant. It operates by shining excitation light of a selected wavelength on cervical tissue and measuring fluorescent emissions. The measurement is completed in seconds. This method is an excellent fit with the clinical needs for determining the status of cervical dilation.

13 Claims, 10 Drawing Sheets

OTHER PUBLICATIONS

Chwalisz, et al., "Progesterone Control of Cervical Ripening—Experimental Studies with the Progesterone Antagonists Onapristone, Lilopristone and Mifepristone", *The Extracellular Matrix of the Uterus, Cervix and Fetal Membranes: Synthesis, Degradation and Hormonal Regulation*, chapt. 12, pp. 119–131, (1991), Leppert and Woessner, Jr., ed., Perinatology Press, Ithaca, N.Y.

Leppert and Yu, "Three-Dimensional Structures of Uterine Elastic Fibers: Scanning Electron Microscopic Studies", *Connective Tissue Res.*, 27:15–31, 1991.

Liu, et al., "Effects of Self-Absorption by Hemoglobins on the Fluorescence Spectra from Normal and Cancerous Tissues", *Lasers in Life Sciences*, 3(3):167–176, 1990.

Liu, et al., "Raman, fluorescence, and time-resolved light scattering as optical diagnostic techniques to separate diseased and normal biomedical media", *Photochem. Photobiol. B: Biol.*, 16:187–253, 1992.

Lohmann, et al., "Native fluorescence of the cervix uteri as a marker for dysplasia and invasive carcinoma", *Eur. J. Obstet. & Gynecol. and Reprod. Biol.*, 31:249–253, 1989.

Osmers, et al., "Collagenase activity in the cervix of non-pregnant and pregnant women", *Arch. Gynecol. Obstet.*, 75–80, 1990.

Ramanujam, et al., "Fluorescence Spectroscopy: A Diagnostic Tool for Cervical Intraepithelial Neoplasia (CIN)", *Gynecol. Oncol.*, 52:31–38, 1994.

Wong, et al., "Infrared spectroscopy of exfoliated human cervical cells: Evidence of extensive structural changes during carcinogenesis", Proc. Natl. Acad. Sci. USA, 88:10988–10992, 1991.

METHOD FOR THE DIAGNOSIS OF CERVICAL CHANGES

BACKGROUND OF THE INVENTION

The invention relates to a non-invasive method for detecting changes in cervical connective tissue using light-induced native fluorescence spectroscopy. More exactly, this invention relates to a procedure useful for determining changes in cervical tissues by recording connective tissue intrinsic fluorescence signals from the cervix of females using light-induced native fluorescence spectroscopy. The extent and progress of such changes relate to maternal readiness for fetal delivery and may be used to diagnose slow progress of labor or other complications.

The cervix is composed almost entirely of connective tissue comprising collagen and macromolecular components which make up the extracellular matrix of this tissue. Many biochemical studies show that there are changes in cervical connective tissue during cervical ripening and dilation during labor. Collagen degradation resulting from increased collagenase activity may be a major element in cervical changes associated with labor. Therefore, an instrument or procedure for instantly and non-invasively measuring these changes would be of great benefit to objectively evaluate the state of the cervix during labor.

Fluorescence spectroscopy is a widely utilized research tool in the biosciences (Udenfriend, 1962), primarily because of the amount of information that it can reveal in terms of molecular physical states (Cantor and Schimmel, 1980). Fluorescent spectra offer important details on the structure and dynamics of macromolecules and their location at microscopic levels (Lakowicz, 1986).

Native fluorescence from intrinsic fluorophors in tissues and cells provides a basis for diagnostic techniques relating to certain diseases (Glassman, 1993). The intrinsic fluorophors, functioning as part of the unique but complicated biological system, change along with the status of cells and tissues. When appropriately applied, tissue fluorescence can provide the medical and veterinary medical fields with a minimally invasive yet highly accurate diagnostic technique. This fluorescence technique has been found to be useful for distinguishing some of the physiological states of abnormal tissues as compared to the corresponding normal tissues (Alfano and Yao, 1981; Alfano et al., 1984; Alfano et al., 1984; Alfano et al., 1987; Alfano et al., 1991). For example, studies have observed differences in the laser or other light-induced native fluorescence spectra between normal tissues and neoplastic tumors in several types of the organs (Tang et al. 1989; Glassman et al. 1991; Cothren et al. 1990; Richards-Kortum et al., 1991; Deckelbaum, et al. 1989; Ma et al., 1990; Glassman et al., 1984). Similar studies have also been done to determine diseased states such as malignancies and dysplasia with human reproductive organs such as cervix, ovary, and uterus (Glassman et al., 1991; Glassman et al., 1994), however this technique has not been applied before to the diagnosis of cervical ripening during pregnancy.

Presently there is no objective manner to evaluate cervical changes associated with dilation and effacement of the cervix during pregnancy. During pregnancy the cervix is normally firm and closed. At the end of pregnancy the cervix becomes softer and dilates as the uterine contractions increase during labor. However, there are many times when the cervix fails to dilate with advancing labor or when the cervix dilates prematurely, prior to labor. The attending physician currently monitors progress of the cervix by visual inspection or by manual examination. However, these subjective tests are often inadequate and vary from physician to physician. An instrument or procedure to more accurately measure cervical changes associated with labor would be invaluable to the diagnosis of cervical problems such as premature dilation or prolonged labor and fetal distress due to delayed cervical dilation.

The present invention provides, for the first time, the ability to accurately and quantitatively determine the status of cervical dilation during pregnancy, and particularly during the last stages of pregnancy and during labor. Differences in the intrinsic fluorescence spectra from the irradiated cervix are observed and compared at various time points during pregnancy and during labor, giving the physician, veterinarian or research scientist instant knowledge of the status of the cervix and cervical opening of an animal or human subject. This knowledge is important for determination of proper treatments. The present invention offers a great improvement over manual palpation and subjective estimation of cervical status as currently practiced. Use of the method described herein will enable safer and more accurate diagnoses concerning the preparation or lack thereof of a prenatal human or animal patient for delivery and recovery.

SUMMARY OF THE INVENTION

The present invention relates to a method and instrumentation for detecting the physiological and biochemical changes in cervical connective tissues associated with various stages of pregnancy, labor, delivery and recovery. This method uses an optical system comprising laser or other light induced native fluorescence spectroscopies (LIF) from the cervix for monitoring these changes. The method is non-invasive and instant. It operates by shining excitation light of a selected wavelength on the cervix and measuring fluorescent emissions. The measurement is completed in seconds and a decrease in fluorescence or other relative changes in the fluorescence spectral profiles indicates dilation progress. This method fulfills an immediate clinical need for determining the status of cervical dilatation during labor.

In more detail, the present invention involves a method for measuring relative cervical dilation to follow the state of labor and anatomical readiness for fetal delivery. In addition, the method can be used to monitor effacement, the obliteration of the cervix in labor when it is so changed that only the thin external os remains. This method comprises irradiating cervical tissue with excitation light in an amount and at a wavelength sufficient to excite intrinsic fluorophors in cervical connective tissue to fluoresce. The measurement of the fluorescent emissions from the irradiated cervical tissue is utilized to monitor changes in the state of cervical dilation, with a decrease in fluorescence indicating an increase in cervical dilation. The excitation light is preferably ultraviolet, more preferably from 300 to 380 nm, and even more preferably between 315 and 350 nm. By ultraviolet is meant light of wavelengths just shorter than visible light. However, it is understood that any excitation wavelength that induces intrinsic fluorescence in the cervical tissue without causing harm to said tissues is acceptable in the practice of the invention. Fluorescent emissions measured are from 340 to 700 nm, more preferably from 340 to 500 nm, and may vary according to the excitation wavelength.

An instrument for measuring cervical tissue fluorescence from the surface is described. Such an instrument comprises an excitation means capable of producing light in the wavelength range from 300 to 380 nm. Such means includes a lamp or laser, as well as appropriate gratings, prism, lenses and/or filters. Any light source with grating, prism with selection slit and/or optical filters and lens that will produce a narrow band or even a monochromatic excitation light spectrum between about 300 nm to about 380 nm is suitable for the present invention. A preferred embodiment comprises a Xenon lamp and a narrow band 340 nm filter associated with a lens, however other light sources and means that produce the preferred excitation light would also be acceptable. Other exemplary light sources might include, but are not limited to mercury lamps, selected monochromatic laser lights, for example, argon-ion lasers, pulsed nitrogen lasers, pulsed Ti:sapphire lasers and the like. It is also understood that any other light source yielding adequate amounts of the necessary wavelengths of light, either directly or after appropriate filtering, or through grating or prism or other optical systems, to excite connective tissue compositions to fluoresce may be used.

Light from the source is transmitted through an optical fiber system so that the cervical tissue may be irradiated. Fluorescent light from the irradiated tissue is collected via a second optical fiber, or optical fiber bundle, that transmits fluorescent light through the appropriate lenses and filters, or grating or prism system, to a means for measurement and/or spectral analysis. The means for measurement includes various optical sensing systems well known to those of skill in the art, such as optical multichannel analysis, charge-coupled devices or photomultiplier tubes, for example. Spectral analysis is accomplished by comparing the measured fluorescence intensities, fluorescence spectral profile changes, and/or the changes in the ratios of the fluorescence intensities at different wavelengths.

The instrument of the present invention may further comprise a small optical catheter suitable for use in a human patient. Such a catheter comprises a means for holding optical fiber bundles such that the tips of said bundles may be placed near the cervix, by for example, insertion of the catheter into the vagina. The catheter may further comprise an endoscope to aid the practitioner in locating the catheter near the cervix.

DETAILED DESCRIPTION OF THE PREFERRED EMBODIMENTS

The present invention concerns an instrument and procedure for measuring cervical changes to objectively evaluate the state of the cervix before during or even after labor. Such objective evaluation has not been possible before the present invention.

It is extremely important for obstetricians to evaluate cervical changes associated with dilation during pregnancy, especially by a non-invasive and rapid method. The close monitoring of the cervical change is important for determination of proper treatments. Optical methods using fluorescence spectroscopy and optical fiber technology may be used to evaluate connective tissues changes in the reproductive system. The method is based on changes in fluorescence spectra of the cervix due to cervical tissue alterations during dilation in labor.

Figure 1:
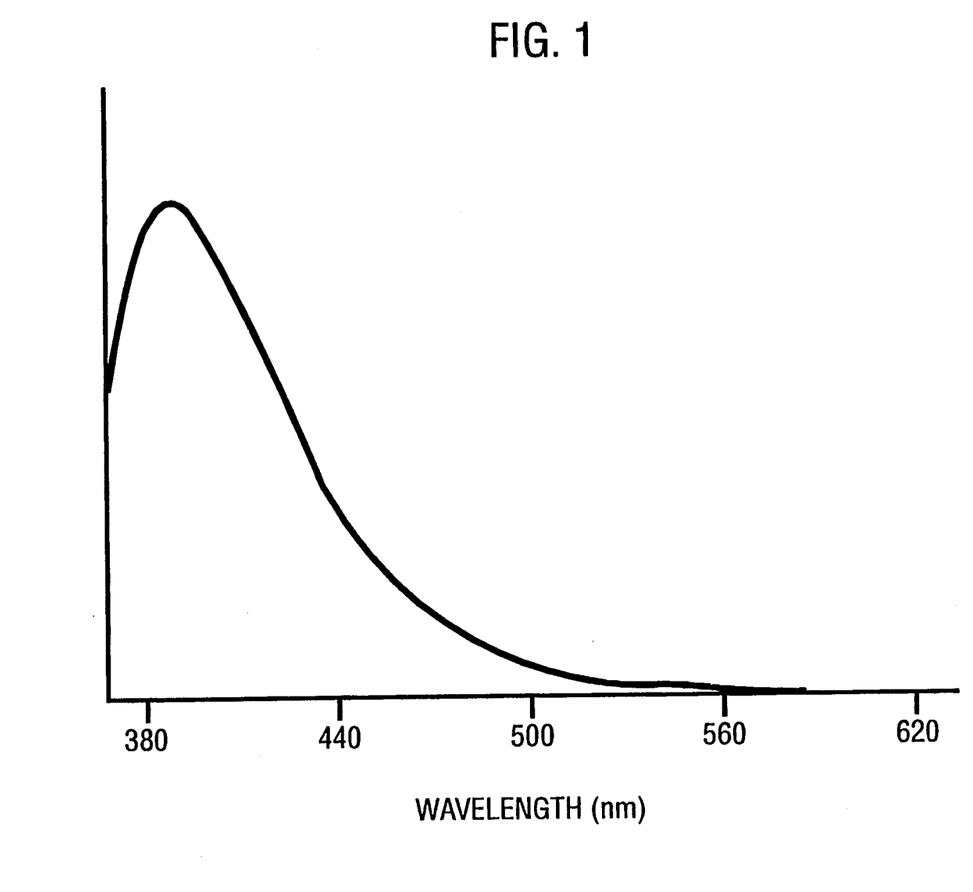
FIG. 1. Fluorescence spectrum of collagen when excitation wavelength is 351 nm.

The cervix contains connective tissue comprising collagen and macromolecular components that make up the extracellular tissue matrix (Fosang et al) and there are biochemical changes in cervical connective tissue during cervical ripening and dilation during labor (Fosang et al.; Granstrom et al., 1989). Collagen degradation from increased collagenase activity associated with labor, may be a major element in cervical changes (Osmers et al., 1990; Kokenyesi and Woessner, 1991). Collagen presents a characteristic fluorescence spectrum as shown in FIG. 1 (Glassman, 1993). The fluorophors in the collagen are identified as pyridinoline, a 3-hydroxypyridinium ring derived from three residues of hydroxylysine. Pyridinoline plays a role in crosslinking the collagen fibers (Eyre et al., 1984).

Connective tissue changes of the reproductive system in pregnancy and during labor may be monitored by measuring native fluorescence spectra. The native fluorescence spectra from the cervix of pregnant rats demonstrate such monitoring. The fluorescence spectra from the cervix of pregnant rats in the process of labor were measured. Differences were found between fluorescence spectra from pregnant rats and from pregnant rats in labor. Cervical dilation is accompanied by a decrease in fluorescence around certain wavelengths. Therefore, cervical dilation may be monitored by a comparison of intrinsic fluorescence from the cervical tissue over the course of time, with a decrease in fluorescence indicating cervical dilation.

A preferred method of quantifying these differences is by comparing the fluorescence peak intensity at about 390 nm either by its absolute fluorescence intensity and/or by its relative fluorescence intensities compared to the intensities at other wavelengths or from other objects. These differences may be observed when exciting tissue with a light source (laser or lamp). Detection and measurement of fluorescence is preferably accomplished with filters, a monochromator, an OMA or CCD camera, or photomultiplier tubes and a computer system with display and print or platter. This method preferably uses optical fibers to deliver the excitation light and to collect fluorescence signals.

The excitation light source can be in the wavelength range of 315 nm to 380 nm, produced by a lamp with selective filters or selective means with grating or prism, or lasers which have output wavelength in this range. A preferred lamp is a Xenon lamp. Fluorescence intensity is preferably measured from 320 nm to 700 nm, which can be varied according to the excitation light. The fluorescence wavelength is always greater than the excitation wavelength.

The following examples are included to demonstrate useful embodiments of the present invention but are not intended to limit the scope of this invention unless otherwise specified in the claims.

EXAMPLE 1

Optical Spectroscopy Methods

Figure 2:
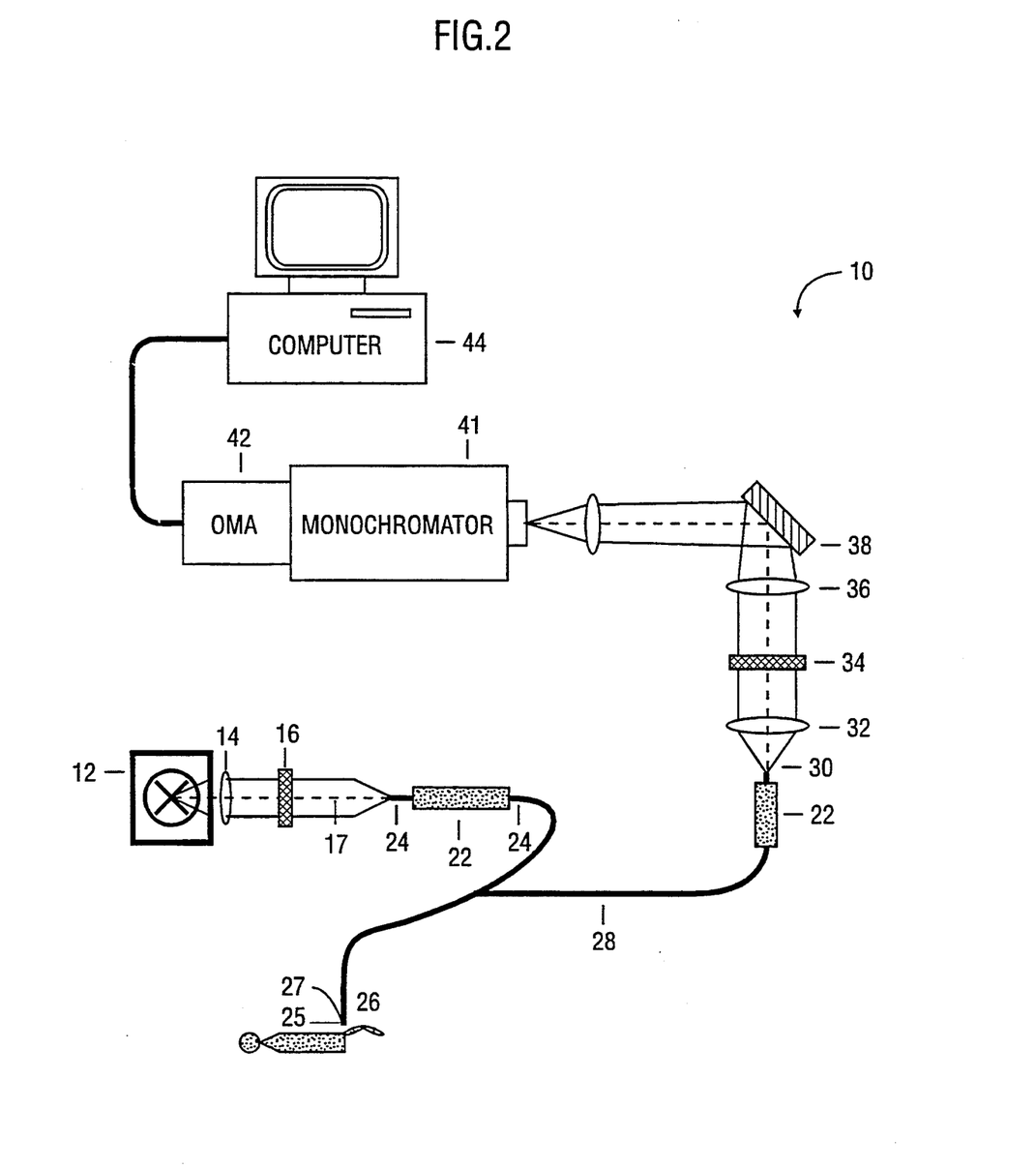
FIG. 2. A schematic of instrumentation for measuring the cervix fluorescence spectra.
Figure 3:
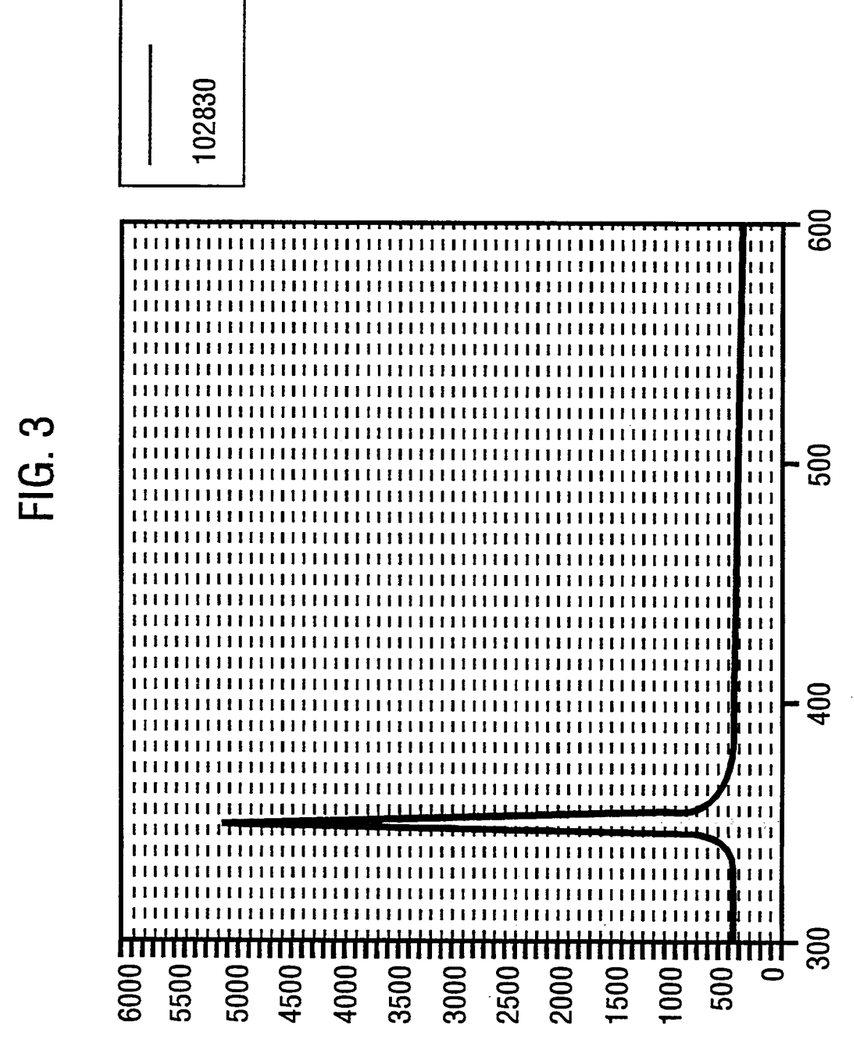
FIG. 3. An exemplary excitation light spectrum.

The equipment 10 used in the fluorescence spectral measurement of rat cervix is schematically shown in FIG. 2. The excitation light source 12 is a xenon lamp (Type No. L2274, with power supply (150W-GS) Model C2499-01, HAMAMATSU PHOTONICS). Light passes through an ACS lens 14 (Newport Corporation) placed in front of the light house with a ground glass window to collect the light. The excitation wavelength is selected with a narrow band optical filter 16 with center wavelength at 340 nm (Model No. 53390, Orial Corp., P.O. Box 872, Stratford, Conn. 06497-9988). The selected light 17 is focused through a fused silica lens 18 (ESCO Products, Inc. f=2.5 cm) at one end 19 of an optical fiber 24 (Model Number HCG-M0550T-10, Ensign-Bickford Optics Company, 150 Fisher Drive, Avon, Conn. 06001) held in an optical fiber holder 22 for delivery of excitation light. The ground glass window and the 340 nm narrow band filter shaped the excitation light spectrum as a narrow peak centered at 348 nm with band width of 5 nm (as shown in FIG. 3). The excitation light 17 delivered through the fiber 24 to the fiber tips 25 and irradiates the measured site 26. The light power at this point is about 12 $\mu$W. The fluorescence emission light is collected by the tips 27 of a second optical fiber 28 (Ensign-Bickford Optics Company, 150 Fisher Drive, Avon, Conn. 06001). The other end 30 of collecting fiber 28 is located at the focus point of a BK7 glass lens 32. The collected signals are transmitted through a long path color glass filter 34 (0–51, ESCO products Inc.) with cut off wavelength at 360 nm (1% transition at this wavelength), focused by an achromatic lens (PAC 052, Newport, Conn.) 36, off a mirror 38 into a grating monochromator 40 (1200 G/mm, Instruments SA, Inc., 173 Essex Avenue, Metuchen, N.J. 08840). The spectra are then recorded by an optical multichannel analyzer 42 (OMA) (Model 1460, EG & E Princeton Applied Research, 6 DeAngelo Drive, Bedford, Mass. 01730). The time required for taking a complete spectrum is less than 10 seconds. This time may be greatly reduced by the use of a more sensitive recording system such as CCD camera 44. A charge-coupled device (CCD) camera would also make it possible to monitor the signal changes on a real time basis. The spectra measuring time can be decreased if the excitation light power increases. However, for in vivo applications, it is better to use low light power and more sensitive detection devices.

In the example below, the excitation light fiber 52 tip 55 and the emission light fiber 53 tip 55 were placed at 15 degree angles. The tips were kept the same distance of 1 mm away from the measuring site of the tissue. A catheter design is also disclosed (FIG. 12) that is suitable for applications in human patients.

EXAMPLE 2

Measuring Native Fluorescence Spectra from Rat Cervix in vivo

Methods

Rats were anesthetized with IP injection of Ketamine HCI/Xylazine (15 mg/2 mg). Dissection was performed to open abdomens of the rats in order to allow optical fiber tips to reach the cervix. The measurements were performed in vivo on various locations of the middle band of the cervix.

A total of 37 rats at various stages of gestation and the labor process were used in this example. Rats were separated into 9 groups as shown in Table 1 (which indicates the number of rats and total points of measurement). The groups were first divided according to the days of pregnancy: 15 days (d15), 17 days (d17), 19 days (d19), 20 days (d20) and 21 days (d21). At term, on day 22 of pregnancy, there were three groups: nondelivery (d22nd), pup engaged, i.e. in the birth canal (d22eng) and at delivery with 2–3 pups delivered (d22del).

There is a second group (d17RU) of rats at 17 days of pregnancy. These rats were treated with IP injection of vehicle (castor oil & benzoyl benzoate) plus RU 38.486 (10 mg per rat) at 16 days of pregnancy, and measured approximately 24 hours later. RU 38.486 is a progesterone receptor antagonist that is used as an abortifacient and contraceptive. RU 486 is the popular name for mifepristone and RU 38.486 is the popular name for mifegyne, 11$\beta$-[4-(N,N-dimethylamino)phenyl]-17$\alpha$-(prop-1-ynyl)-$\Delta^{4,9}$-estradiene-17$\beta$-ol-3-one. Administration of RU 38.486 induces cervical softening and preterm delivery. This effect of the drug would also result in cervical changes similar to those seen in normal labor and delivery. Therefore, RU 38.486 is a positive control for the methods disclosed herein.

The physiological change in the cervix can be clearly observed after dissection, even though the pups were not clearly engaged. In contrast, one control rat was IP injected at day 16 with only the vehicle (castor oil & benzoyl benzoate) and the measurement was performed 24 hours later on day 17. This rat showed the spectra similar to the untreated rats on day 17, and was therefore grouped with d17.

TABLE 1

| Stages | List of the Groups of Rats and Measurements | | | | | | | | |
|---|---|---|---|---|---|---|---|---|---|
|  | D15 | D17 | D19 | D20 | D21 | D22nd | D22eng | D22del | D17RU |
| No. of Rats | 4 | 3 | 4 | 4 | 6 | 4 | 4 | 3 | 4 |
| Total No. of | 10 | 8 | 10 | 11 | 19 | 12 | 13 | 11 | 15 |

TABLE 1-continued

| | List of the Groups of Rats and Measurements | | | | | | | | |
|---|---|---|---|---|---|---|---|---|---|
| Stages | D15 | D17 | D19 | D20 | D21 | D22nd | D22eng | D22del | D17RU |
| Measurements | | | | | | | | | |

Figure 4:
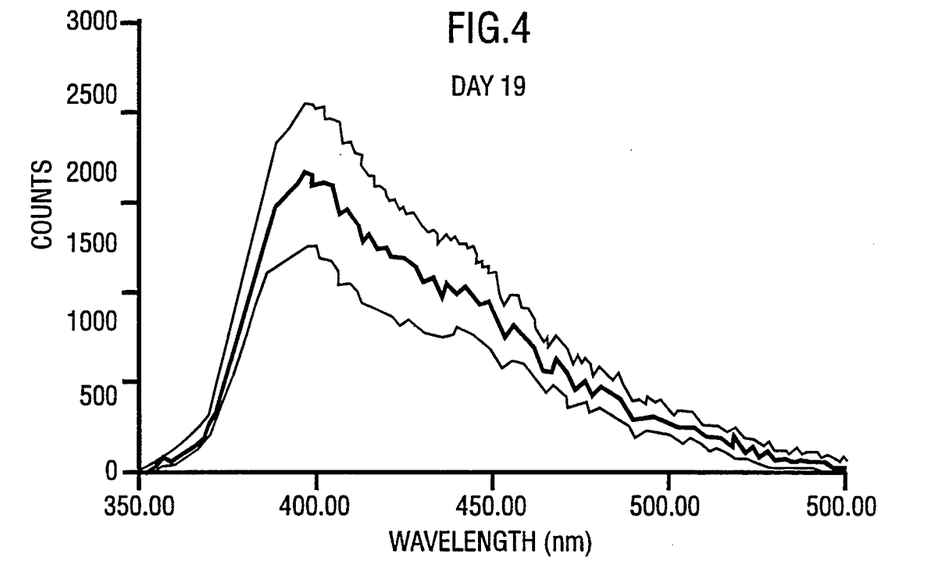
FIG. 4. Average spectrum and the 95% confidence interval from the middle band of cervix of the rats on 19 days of pregnancy.
Figure 5:
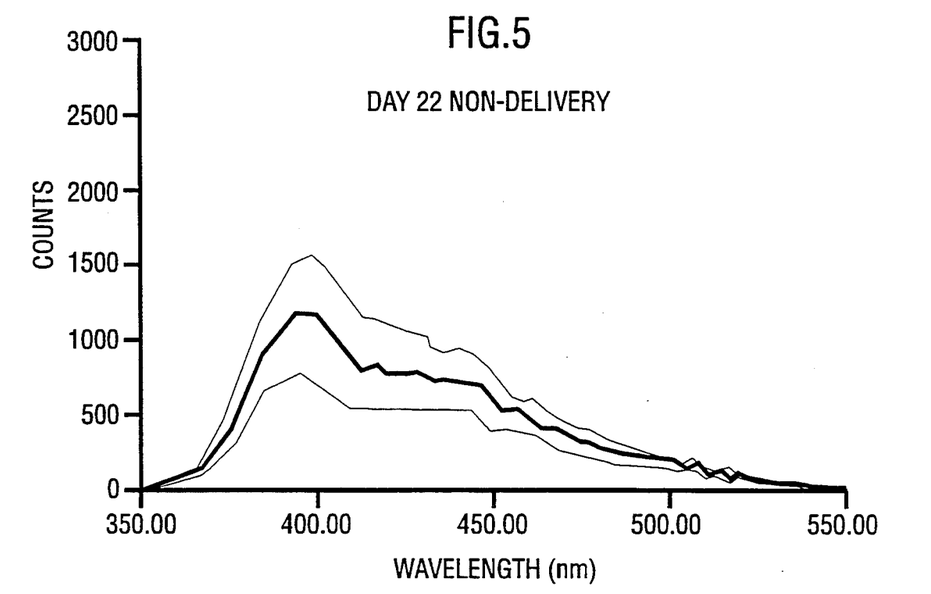
FIG. 5. Average spectrum and the 95% confidence interval from the middle band of cervix of the rats on 22 days of pregnancy but non-delivery.
Figure 6:
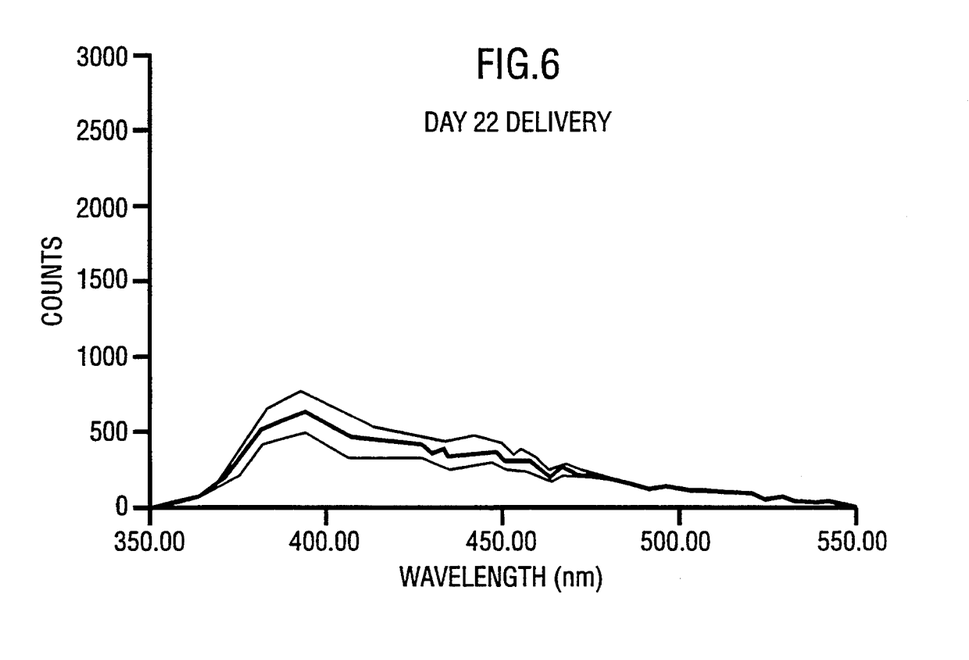
FIG. 6. Average spectrum and the 95% confidence interval from the middle band of cervix of the rats on 22 days of pregnancy and in delivery.
Figure 7:
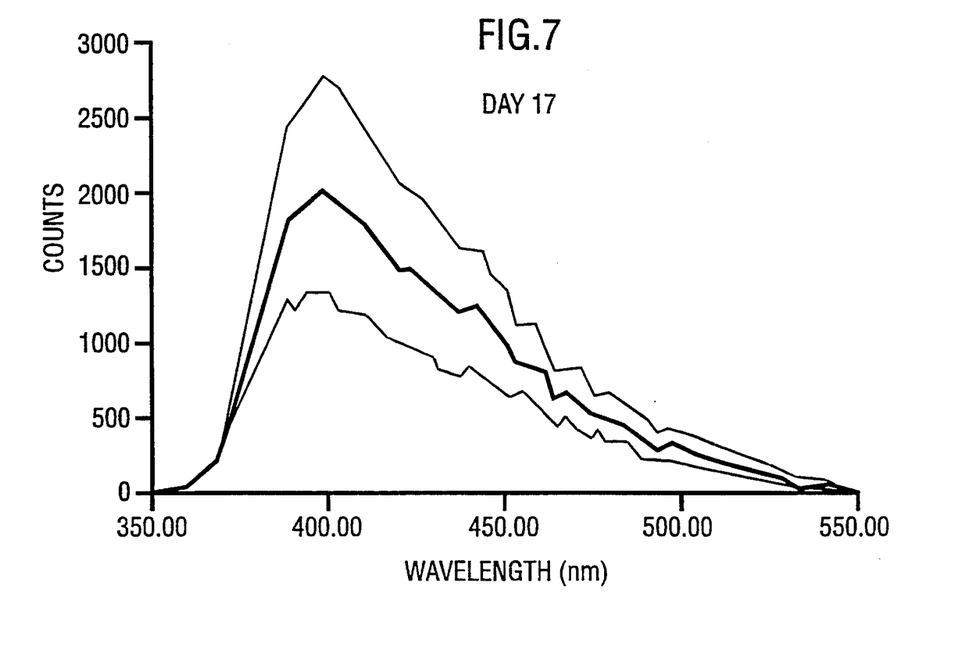
FIG. 7. Average spectrum and the 95% confidence interval from the middle band of cervix of the rats on normal 17 days of pregnancy.
Figure 8:
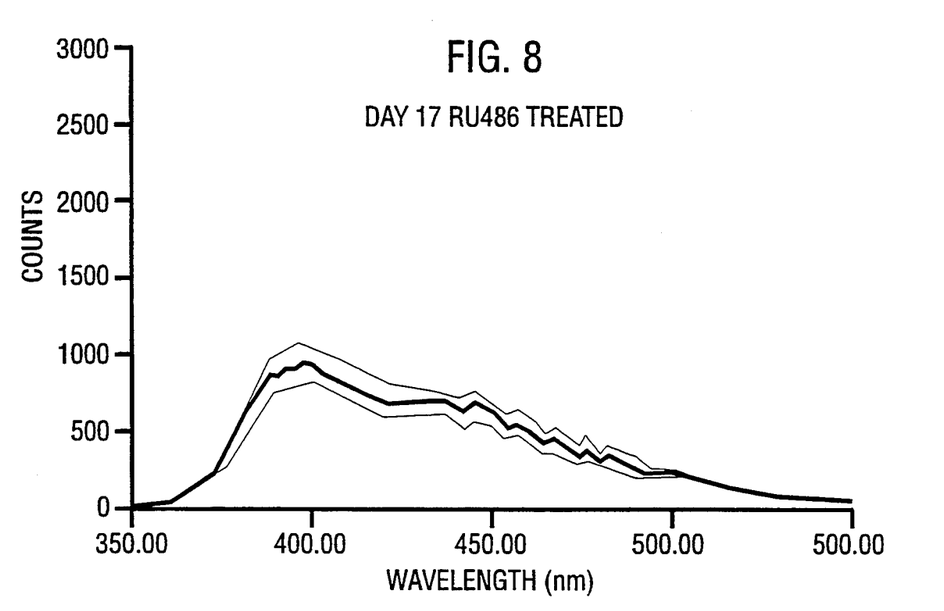
FIG. 8. Average spectrum and the 95% confidence interval from the middle band of cervix of the rats on 17 days of pregnancy with RU 38.486 treatment.

There were clear changes in the fluorescence intensities but small fluorescence profile changes in the tested groups. The average spectra and its 95% confidence margin from the cervix on gestational day 19, day 22 non-delivery and day 22 delivery are shown in FIGS. 4, 5 and 6, respectively. The results show a significant decrease in intensities from day 19 to day 22 nondelivery, and from day 22 non-delivery to day 22 delivery. The average spectra and its 95% confidence margin from the rats on day 17 and the rats on day 17 treated with RU 38.486 are shown in FIGS. 7 and 8, respectively. The fluorescence intensity also shows significant decrease from normal pregnant day 17 rats to day 17 RU 38.486 treated rats.

Figure 9:
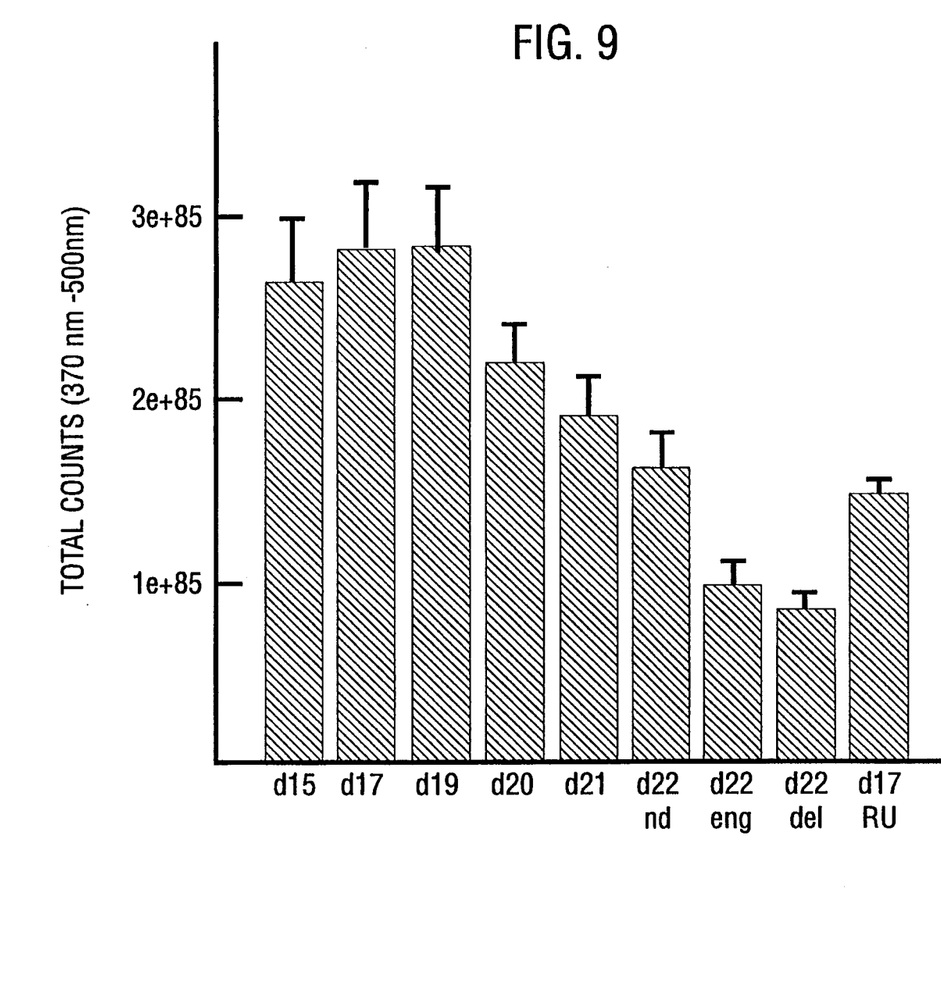
FIG. 9. Total fluorescence counts between wavelength range 370 nm to 500 nm versus different stages of gestation. Error bars indicate the Mean±SEM.

Total counts of each measurement of fluorescence from the wavelength range 370 nm to 500 nm have been calculated and analyzed for statistical significance. The mean with SEM of each group at different stages of gestation are shown in FIG. 9. The one-factor ANOVA analysis was highly significant ($F = 10.4$, $p < 0.001$). The a priori comparison results between individual groups are shown in Table 2. The total counts integrated within other narrower wavelength ranges, 395 nm to 415 nm for example, have also been calculated. The statistical analysis showed similar results.

The results show the clear changes of the native cervical fluorescence during various stages of gestation with high statistical significance. The amount of fluorescence decreases when the pregnancy is close to term, and reaches its lowest point when pups are engaged and in delivery. RU 38.486 treatment on day 16 of gestation also caused the native fluorescence to decrease. Although the decrease in fluorescence in the RU38.486 treated rats did not reach the levels of decrease in delivering rats, this is simply because the treated rats were not monitored through delivery. Had the treated rats been monitored through delivery, it is understood that the fluorescence would have reached the lower levels observed in untreated delivering rats.

Figure 10:
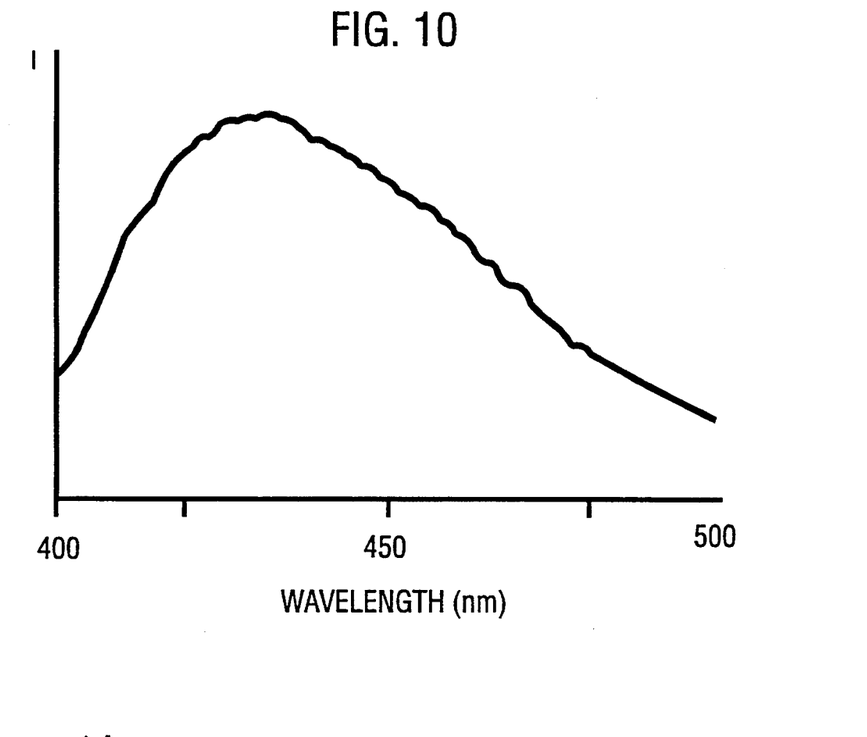
FIG. 10. Fluorescence spectrum of elastin when excitation wavelength is 351 nm.
Figure 11:
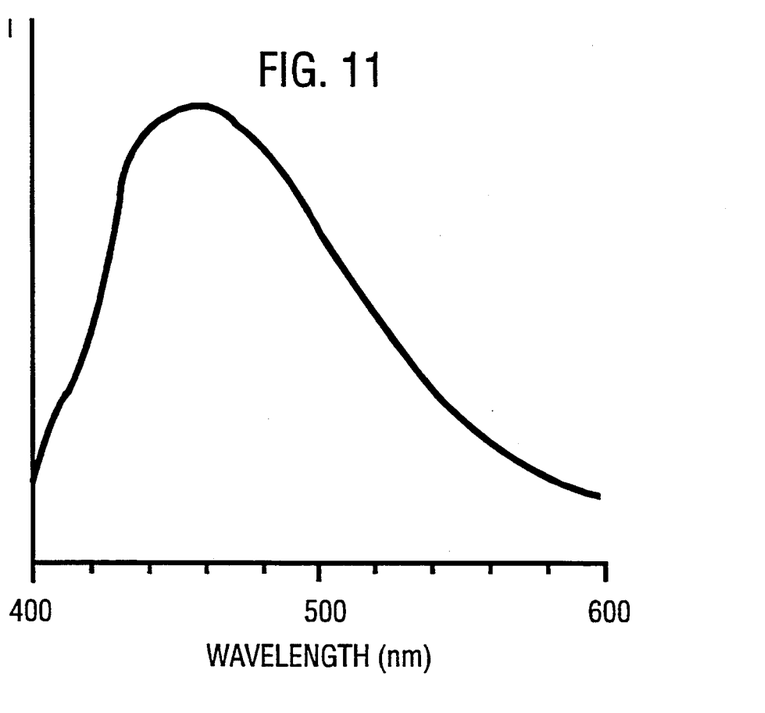
FIG. 11. Fluorescence spectrum of free NADH.

(Leppert and Yu, 1991). There may be some small amount of fluorescence contribution from elastin and NADH which overlap on the collagen spectrum (Glassman et al., 1991; Glassman, 1993). Fluorescence spectra of elastin and NADH are shown in FIGS. 10 and 11, respectively. Generally speaking, collagen fluorescence has a relatively sharp fluorescence peak at 390 nm when the excitation wavelength is close to 350 nm. Free NADH has a fluorescence band with a peak at 460 nm, which is blue shifted to 450 nm when the NADH is in the bound state. Elastin has a wide fluorescence spectrum band with peak at 420 nm when the excitation wavelength is close to 350 nm. In analysis of the fluorescence spectral structure of connective tissues, the peak or shoulder structure at the wavelength range of 380–390 nm are more likely the result of collagen fluorescence. The small fluorescence band at wavelength range 400 nm to 500 nm is more likely the result of elastin and NADH. The dip which sometimes occurs at wavelength 415 nm to 420 nm is caused by the reabsorption of blood (Glassman, 1993; Tang et al., 1989; Liu et al., 1990).

The results described demonstrate the usefulness of this new technique and instrument in the monitoring cervical changes during pregnancy and labor and in determining the physiological or biochemical state of the cervix during the final stages of pregnancy. For a human subject, a small size fiber optical catheter is used. Because the human cervix is also rich in collagen and because the cervix is accessible to the instrument disclosed herein, human cervical dilation may be similarly measured by positioning the optical catheter through the vagina. The particular fluorescent intensities may differ from species to species, but the relative decrease in, e.g., collagen fluorescence, that is monitored over time will allow a more quantitative or objective measurement of cervical changes incipient to birth and will be a valuable diagnostic and prognostic tool in the field of obstetrics.

TABLE 2

| A priori Comparisons Results between Groups (LSD Method). | | | | | | | | | |
|---|---|---|---|---|---|---|---|---|---|
| | D15 | D17 | D19 | D20 | D21 | D22nd | D22en | D22del | D17RU |
| D15 | | | | | * | ** | *** | *** | ** |
| D17 | | | | | * | ** | *** | *** | *** |
| D19 | | | | | ** | ** | *** | *** | *** |
| D20 | | | | | | | *** | *** | * |
| D21 | | | | | | | *** | ** | |
| D22nd | | | | | | | * | * | |
| D22eng | | | | | | | | | |
| D22del | | | | | | | | | * |
| D17RU | | | | | | | | | |

*p-value < 0.05
**p-value < 0.01
***p-value < 0.001

These changes in the native cervical fluorescence may be the result of either or both biochemical and physiological changes of cervical tissues during gestation and labor. As stated above, the general structure of the fluorescence spectra from the cervix seems similar. The fluorescence of the cervix of rats may be mostly contributed by pyridinoline cross-links since the collagen concentration is very high in the rat cervix tissue

EXAMPLE 3

Design of Optical Catheter

Figure 12:
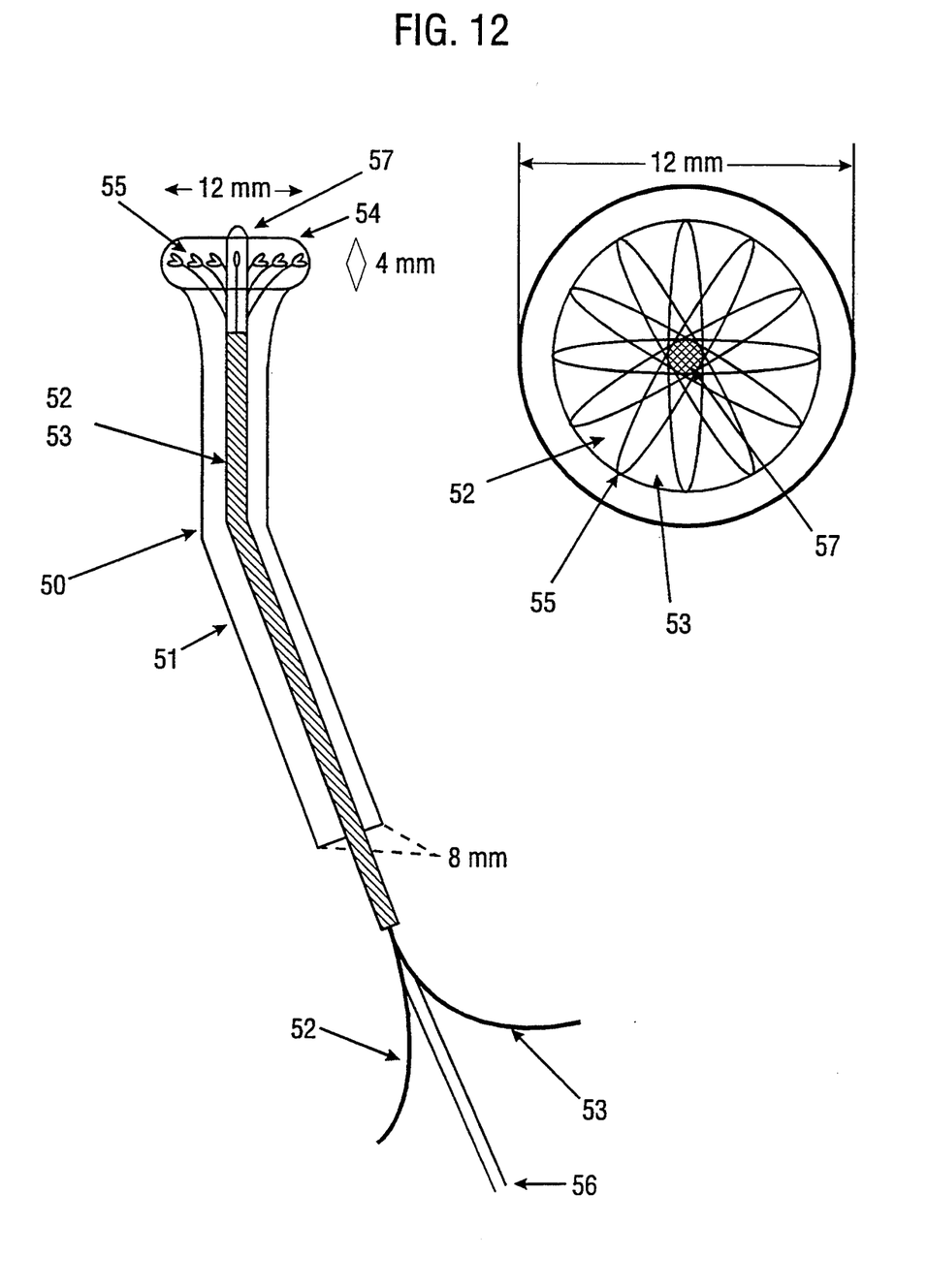
FIG. 12. Schematic diagram of the catheter for use in human patients in a side view and top view.

A preferred embodiment of the present invention is an optical catheter suitable for use in a human patient as schematically shown in a side view and a top view in FIG. 12. The catheter 50 comprises a hollow tube 51 with an outer diameter of about 8 mm or less and forming an obtuse angle near the midpoint for correct positioning. The optical fiber bundles for transmission of the excitation light 52 and the optical fiber bundles for the collection of emission light 53 are disposed within the hollow tube and exit the tube through one end to be connected to the excitation light source and measuring means, respectively. At the other end of the tube is a receptacle 54 of about 4 mm in height and about 12 mm in diameter to receive the tips 55 of the two types of optical fiber bundles and to position the tips adjacent the measuring site on the cervix. The catheter may also comprise an endoscope 56 with an endoscope head 57 projecting past the optical fiber tips to assist in locating the catheter near the cervix.

Figure 13:
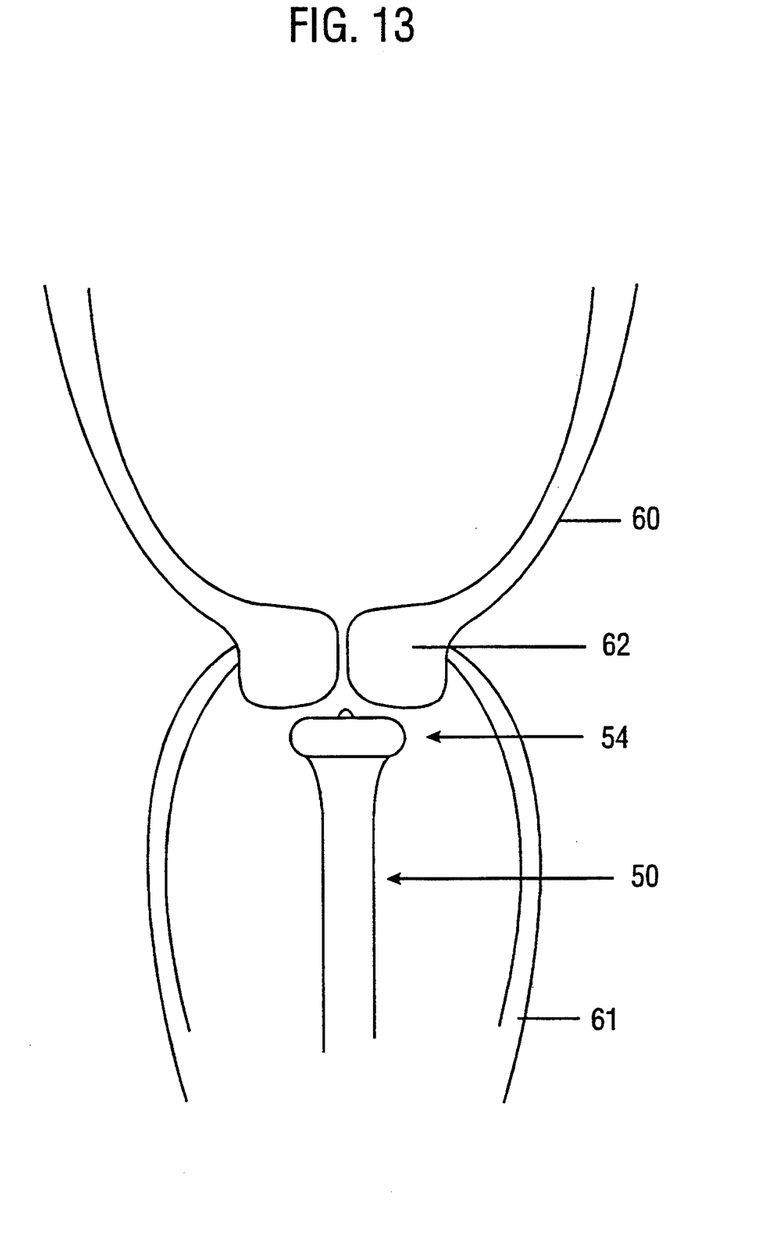
FIG. 13. Schematic diagram of the catheter in place in the vagina of a subject.

FIG. 13 is an illustration of the optical catheter 50 in place in the vagina of a subject. The endoscope 56 facilitates placing the catheter near the cervix 62, which separates the vaginal wall 61 from the uterine wall 60.

EXAMPLE 4

Continuous Monitoring of Human Patient

In an example of a preferred embodiment of the methods and instruments of the present invention, a pregnant patient visits her obstetrician for a routine perinatal exam at e.g., 26 weeks of pregnancy. The physician uses the methods and instruments disclosed herein to evaluate the state of the cervix. The physician inserts the optical fiber probe (FIG. 12) into the vagina of the patient after dilating the vagina with the aid of a speculum to expose the cervix. Several regions of the cervix are probed and fluorescence spectra are obtained. These spectra are compared to known normal and abnormal readings.

This procedure is repeated during weekly or bimonthly visits to the obstetrician. At term, about 38 to 40 weeks of gestation, the physician makes more frequent analyses with the described methods. When the patient is admitted to the hospital in labor or where labor is imminent, the instrument and methods are used at hourly intervals to evaluate the cervix and the progression of dilation.

If the patient begins to show signs of preterm dilation of the cervix, the physician may treat the patient with an agent (e.g. an antiprostaglandin) to inhibit cervical dilation and then may follow the progress of this treatment with the methods disclosed herein. If a patient fails to dilate at term with advancing uterine contractions, the physician may stimulate cervical dilation (e.g. with a prostaglandin) and follow the progress of the induced dilation with the methods of the invention.

It is also understood that certain problems may arise in recovery after delivery. In that case, the cervical monitoring may continue during the period of postpartum recovery to assist in diagnosis and treatment of any conditions that may arise.

EXAMPLE 5

Monitoring Patients at Term or Preterm Delivery

In this example, a patient appears in labor and delivery either at term or preterm in labor. A physician quickly evaluates the patient's cervix with the methods of the present invention to determine the extent of dilation and then follows the patient continuously until delivery as in Example 4.

EXAMPLE 6

Non-pregnant Patient

A nonpregnant patient, age about 40 years for example, may require a dilation and curettage (D&C) for abnormal uterine bleeding. The physician treats the patient with an agent such as a prostaglandin to dilate the cervix and then follows the progression of cervical dilation with the methods disclosed herein. At the appropriate time, as indicated by the fluorescence spectra, the curettage of the uterine wall is completed.

EXAMPLE 7

Monitoring of Animal Patients

The present example demonstrates that the methods and instruments of the present invention will also be useful in the treatment and monitoring of animals. A veterinarian is called upon to monitor the delivery of a valuable animal such as a horse, cow, dog or the like that is in labor, but is suffering from dystocia (i.e. the inability for labor to progress). The practitioner examines the cervix of the animal with the methods and instruments of the present invention. The practitioner may then either treat the animal appropriately with a labor accelerating agent such as oxytocin or prostaglandin, or may abstain from treatment and follow the progression of the cervix with the disclosed methods.

The following citations are incorporated by reference in pertinent part herein for the reasons cited in the above text.

Alfano, R. R. and Yao, S.S. Journ. Dent. Res. 60:120-122, 1981.

Alfano, R. R., et al., IEEF J. of Quant. Elec. QE-20:1512-1516, 1984.

Alfano, R. R., et al., Laser induced fluorescence spectroscopy from native cancerous and normal tissues, *IEEE J. of Quant. Electron.* QE-20:1507, 1984.

Alfano, R. R., et al., *IEEE J. Quantum Electron.* QE-23:1806-181, 1987.

Alfano, R. R., et al., *Bull. N.Y. Acad. Med.*, second series, 67(2):143, 1991.

Cantor, C.R., and Schimmel, P.R., *Biophysical Chemistry*, W.H. Freeman and Company, New York, 1980.

Cothren, R.D., et al., *Gastrointestinal Endoscopy*, 36(2):105, 1990.

Deckelbaum, L.I., et al., *Lasers in Surgery and Medicine*, 9:205-214, 1989.

Eyre, D.R., et al, Quantitation of Hydroxypyridinium Crosslinks in Collagen by High-Performance Liquid Chromatography, *Analytical Biochemistry*, 137:380-388, 1984.

Eyre, D.R., Paz, M.A., Gallop, P.M., Cross-linking in Collagen and Elastin, *Ann. Rev. Biochem.* 53:717-48, 1984.

Fosang, A.J. and Handley, C.J., Connective Tissue Remodeling in the Ovine during Pregnancy and at Term, *Connective Tissues Research*, 17:277-285, 1988.

Fujimoto, D., Akiba, K., Nakamura, N., Biochem. *Biophysics Res. Commun.* 76:1124-29, 1977.

Glassman, W. S., Thesis, Graduate Center of city University of New York, 1993.

Glassman, W. S., et al., Excitation Spectroscopy from Malignant and Non-malignant Gynecological Tissues, *Lasers in the Life Sciences*, 6(2), 1994.

Glassman, W. S., et al, Lasers in the Life Sciences, 5(1-2):4958, 1991.

Granstrom, L., et al, Changes in the Connective Tissues of Corpus and Cervix Uteri during Ripening and Labour in term Pregnancy, *British Journal of Obstetrics and Gynaecology*, 96:1198–1202, 1989.

Granstrom, L., Ekman, G., Malmstrom, A., Insufficient remodelling of the uterine connective tissues in woman with protracted labor, *British J Obstet Gynecol*, 98:1212–1216, 1991.

Gunja-Smith, Z. and Woessner, J.F., Content of the collagen and elastin cross-links pyridinoline and desmosines in the human uterus in various reproductive states, *Am J Obstet Gynecol*, 153:92–95, 1985.

Gunja-Smith, Z., Lin J., Woessner, J.F., Changes in Desmosine and Pyridinoline Cross-links During Rapid Synthesis and Degradation of Elastin and Collagen in the Rat Uterus, *Matrix*, 9:21–27, 1989.

Kapadia, C.R., et al, *Gastroenterology*, 99:150, 1990.

Kokenyesi, R. and Woessner, J.F., Relationship between dilatation of the rat uterine cervix and a small dermatan sulfate proteoglycan, *Biology of Reproduction*, 42:87–97, 1990.

Kokenyesi, R., and Frederick Woessner, J., Effects of Hormonal perturbations on the Small Dermatan Sulfate Proteoglycan and Mechanical Properties of the Uterine Cervix of Late Pregnant Rats, *Connective Tissue Research*, 26:199–205, 1991.

Lakowicz, J.R., Principles of Fluorescence Spectroscopy, 3rd print, Plenum Press, 1986.

Leppert, P.C. and Yu, S.Y., Three-dimensional structures of uterine elastic fibers: scanning electron microscopic studies, *Connective Tissue Research*, 27:15–31, 1991.

Liu, C.H., et al., *Lasers in Life Science*, 3(3):167, 1990.

Ma, P.Z., et al., Appl. *Lasers*, 4:235–238, 1984.

Osmers, R., et al., Collagenase Activity in the Cervix of Nonpregnant and Pregnant Women, *Arch. Gynecol. Obstet.*, 248:75–80, 1990.

Richards-Kortum, R., et al., *Photochem. & Photobiol.*, 53(6):777, 1991.

Tang, G.C., et al., Spectroscopic differences between human cancer and normal lung and breast tissues in *Lasers in Surg. and Med.*, 9:290–295, 1989.

Tang, G.C., et al., Pulsed and CW laser fluorescence spectra from cancerous, normal, and chemically treated normal human breast and lung tissues, Appl. Opt. 28(12):2337–2342, 1989.

Udenfriend, S., *Fluorescence Assay in Biology and Medicine*, Vol. I, Academic Press: New York, 1962.

What is claimed is:

1. A method for determining occurrence of cervical dilation or effacement of a subject, the method comprising:
   irradiating cervical connective tissues with excitation light in an amount and at a wavelength causing intrinsic fluorescence; and
   measuring fluorescent emissions from the cervical tissue;
   wherein cervical dilation or effacement is correlated with changes in fluorescent emissions.

2. The method of claim 1 where the excitation light wavelength is ultraviolet.

3. The method of claim 1 where the excitation light wavelength is between about 300 nm and 380 nm.

4. The method of claim 1 where the fluorescent emissions are at a wavelength between about 320 nm and 700 nm.

5. The method of claim 1, wherein the cervical dilation or effacement is measured during pregnancy.

6. The method of claim 1, wherein the cervical dilation or effacement is measured during labor.

7. The method of claim 1, wherein the cervical dilation or effacement is measured in a non-pregnant subject.

8. The method of claim 1, wherein the cervical dilation or effacement is measured after delivery.

9. The method of claim 1, wherein a decrease in fluorescent emission is indicative of cervical dilation or effacement.

10. The method of claim 1 wherein a means for introducing excitation light and for collecting fluorescent emission is introduced through the vagina of a subject.

11. The method of claim 1 wherein the subject is a human.

12. An instrument for measuring cervical tissue fluorescence comprising:
    a means for cervical surface excitation comprising a source of 300 to 380 nm light and optical fiber for guiding the light to a cervical surface;
    a means for measuring cervical tissue fluorescence comprising an optical fiber collection means for transmitting cervical fluorescence to a means for measurement and spectral analysis of said fluorescence
    said optical fiber and optical fiber collection means being disposed in a hollow tube having two ends and forming an obtuse angle between said ends for positioning adjacent a cervical measuring site by manual manipulation of the hollow tube.

13. The instrument of claim 12, further comprising an endoscope to assist in positioning.

* * * * *